United States Patent
Yang et al.

(10) Patent No.: US 11,840,501 B2
(45) Date of Patent: Dec. 12, 2023

(54) XYLITOL PREPARATION DEVICE INTEGRATING EVAPORATION, CRYSTALLIZATION AND CENTRIFUGAL SEPARATION AND CONTROL METHOD THEREOF

(71) Applicants: Zhejiang Huakang Pharmaceutical Co., Ltd., Zhejiang (CN); Zhejiang University, Zhejiang (CN); Zhejiang University of Technology, Zhejiang (CN)

(72) Inventors: Jian Yang, Zhejiang (CN); Yi Zheng, Zhejiang (CN); Taogang Zhang, Zhejiang (CN); Han Gao, Zhejiang (CN); Mian Li, Zhejiang (CN); Zhiqiang Liu, Zhejiang (CN); Yuguo Zheng, Zhejiang (CN); Baoxing Mao, Zhejiang (CN); Xiaojian Zhang, Zhejiang (CN); Weiwei Fan, Zhejiang (CN)

(73) Assignees: Zhejiang Huakang Pharmaceutical Co., Ltd., Zhejiang (CN); Zhejiang University, Zhejiang (CN); Zhejiang University of Technology, Zhejiang (CN)

( * ) Notice: Subject to any disclaimer, the term of this patent is extended or adjusted under 35 U.S.C. 154(b) by 468 days.

(21) Appl. No.: 17/288,020

(22) PCT Filed: Mar. 13, 2020

(86) PCT No.: PCT/CN2020/079365
§ 371 (c)(1),
(2) Date: Apr. 23, 2021

(87) PCT Pub. No.: WO2020/187169
PCT Pub. Date: Sep. 24, 2020

(65) Prior Publication Data
US 2021/0395174 A1      Dec. 23, 2021

(30) Foreign Application Priority Data
Mar. 18, 2019 (CN) .......................... 201910205265.8

(51) Int. Cl.
C07C 29/78 (2006.01)
A23L 27/30 (2016.01)
(Continued)

(52) U.S. Cl.
CPC .............. *C07C 29/78* (2013.01); *A23L 27/34* (2016.08); *B01D 1/26* (2013.01); *B01D 9/0022* (2013.01);
(Continued)

(58) Field of Classification Search
CPC ......... C07C 29/78; C07C 31/18; A23L 27/34; B01D 1/26; B01D 9/0022; B01D 21/262
See application file for complete search history.

(56) References Cited

U.S. PATENT DOCUMENTS 4,246,431 A * 1/1981 Munir .................. C13K 13/002
568/863
5,980,640 A * 11/1999 Nurmi ...................... C13K 5/00
127/60

(Continued)

FOREIGN PATENT DOCUMENTS

CN      108837550      * 11/2018 ........... B01D 9/0031
CN      109761755           5/2019
(Continued)

OTHER PUBLICATIONS

CN 108837550, Guo Xiaopeng et al., Vacuum continuous xylitol crystallization method and system, English translation, 13 pages (Year: 2018).*

(Continued)

*Primary Examiner* — Yate' K Cutliff
(74) *Attorney, Agent, or Firm* — Fish & Richardson P.C.

(57) ABSTRACT

The present invention relates to a xylitol preparation device integrating evaporation, crystallization and centrifugation, including a xylitol tank, a cleaning liquid tank, a recycling tank and a multiple distribution system, wherein the multiple distribution system includes J groups of evaporators for evaporation concentration, K groups of vacuum crystallization kettles for vacuum crystallization and L groups of (Continued)

centrifuges for centrifugation, wherein $2 \leq J \leq 6$, $6 \leq K \leq 12$ and $2 \leq L \leq 4$; the evaporator, the vacuum crystallization kettle and the centrifuge in different groups are sequentially connected in series with one another through a pipeline and a valve respectively; by controlling on and off of each valve, a xylitol exchange liquid is switched and controlled between a series-connection mode and a parallel-connection mode in the multiple distribution system to enable evaporation, crystallization and separation processes to reach an optimal effect distribution so as to improve productivity. The present invention further discloses a control method of the device. The processes and equipment of the present invention are highly integrated to realize continuous integrated production of xylitol preparation with low energy consumption and high automation degree, and full utilization of raw materials.

10 Claims, 1 Drawing Sheet

(51) Int. Cl.
| | | |
|---|---|---|
| *B01D 1/26* | (2006.01) | |
| *B01D 9/00* | (2006.01) | |
| *B01D 21/26* | (2006.01) | |
| *C07C 31/18* | (2006.01) | |

(52) U.S. Cl.
CPC .......... *B01D 21/262* (2013.01); *C07C 31/18* (2013.01); *A23V 2002/00* (2013.01); *B01D 2009/0086* (2013.01)

(56) References Cited

U.S. PATENT DOCUMENTS 5,998,607 A * 12/1999 Heikkila ............. C13K 13/002
568/861
2003/0125588 A1 7/2003 Danisco

FOREIGN PATENT DOCUMENTS

| CN | 209669095 | 11/2019 |
|---|---|---|
| JP | H 11-500913 | 1/1999 |
| JP | 2000-511199 | 8/2000 |

OTHER PUBLICATIONS

PCT International Search Report in International Appln. No. PCT/CN2020/079365, dated Jun. 23, 2020, 5 pages (with English translation).

\* cited by examiner

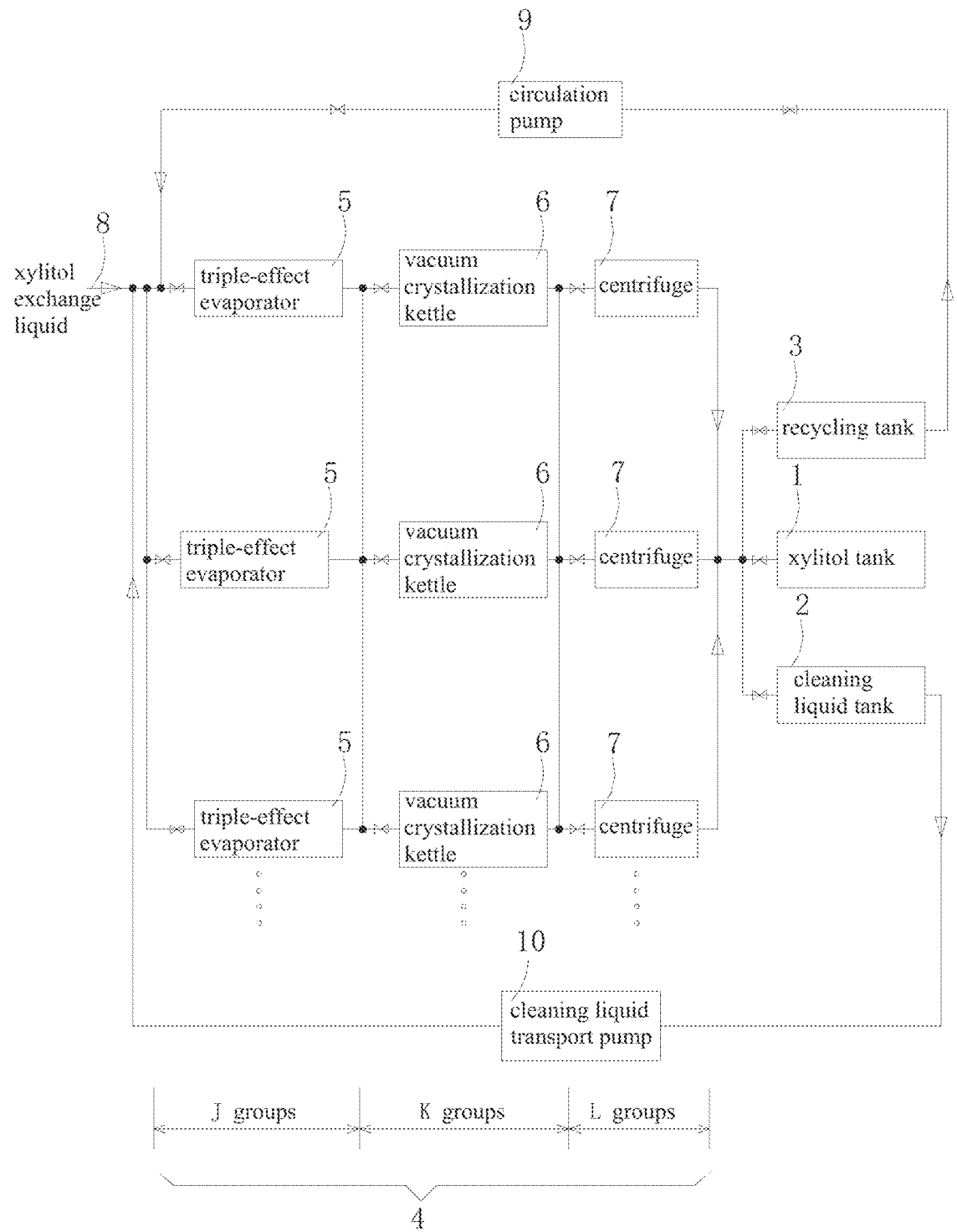

XYLITOL PREPARATION DEVICE INTEGRATING EVAPORATION, CRYSTALLIZATION AND CENTRIFUGAL SEPARATION AND CONTROL METHOD THEREOF

CROSS REFERENCE TO RELATED APPLICATIONS

This application is a national phase filing under 35 U.S.C. § 371 of International Application No. PCT/CN2020/079365, filed Mar. 13, 2020, which claims priority from Chinese Application No. 201910205265.8, filed Mar. 18, 2019. The entire contents of the prior applications are incorporated herein by reference in their entirety.

TECHNICAL FIELD

The present invention belongs to the technical field of food additive production, and particularly relates to a xylitol preparation device integrating evaporation, crystallization and centrifugation and a control method thereof.

BACKGROUND

Xylitol is a pentitol that may be used as a substitute for sucrose. Xylitol is as sweet as sucrose but has only 60% calories of the sucrose. After entering blood, xylitol can penetrate into cells without insulin and is metabolized rapidly without blood glucose increase, and thus the xylitol is a nutritional sugar substitute most suitable for diabetic patients. In addition, xylitol also has effects of improving liver functions, preventing dental caries and reducing body weight, and is a special nutritional sweetener. Due to these properties, xylitol is widely used in the fields of food, medicine, chemicals, and the like, which greatly promotes the development of xylitol industry in China. However, compared with the most advanced enterprises worldwide, sugar industry in China still faces problems such as low-value-added products, large energy consumption, out-of-date equipment and technology, low production efficiency, low automation degree and insufficient deep-processing capacity.

With the prices of automatic control devices gradually dropping and the labor costs increasing year by year, it is more and more obvious to yield economic benefits by reducing man labor by improving automation level. Further, an automatic production line has advantages such as stable control of process parameters, uniform product quality and high product yield, resulting in prominent indirect economic benefits. Therefore, a control method of preparing xylitol by integrating evaporation, crystallization and centrifugation becomes a research hotspot in recent years.

SUMMARY

To solve the technical problems, the present invention provides a xylitol preparation device integrating evaporation, crystallization and centrifugation and a control method thereof to fully utilize raw materials to increase productivity and obtain high purity products while saving energy and reducing emission.

The present invention is realized by providing a xylitol preparation device integrating evaporation, crystallization and centrifugation, including a xylitol tank, a cleaning liquid tank, a recycling tank, and a multiple distribution system. The multiple distribution system includes J groups of evaporators for evaporation-concentrating xylitol exchange liquid to be treated into xylitol concentrate, K groups of vacuum crystallization kettles for obtaining a xylitol paste by vacuum-crystallizing the xylitol concentrate and L groups of centrifuges for obtaining a finished xylitol crystal by centrifuging the xylitol paste, where $2 \leq J \leq 6$, $6 \leq K \leq 12$ and $2 \leq L \leq 4$. Inlets and outlets of the evaporators, the vacuum crystallization kettles and the centrifuges in different groups are sequentially connected in series with one another through a pipeline and a valve respectively. The inlets and the outlets of the evaporators in J groups are connected in parallel with each other through a pipeline respectively, the inlets and the outlets of the vacuum crystallization kettles in K groups are connected in parallel with each other through a pipeline respectively, the inlets and the outlets of the centrifuges in L groups are connected in parallel with each other through a pipeline respectively. The inlet of each evaporator in J groups is in communication with a main pipeline holding the xylitol exchange liquid to be treated through a pipeline and a valve respectively, and the outlet of each centrifuge in L groups is in communication with the xylitol tank, the cleaning liquid tank and the recycling tank through a pipeline and a valve respectively. The xylitol tank is used to collect the prepared xylitol crystal, the cleaning liquid tank is used to collect cleaning liquid from cleaning the evaporators, the vacuum crystallization kettles and the centrifuges respectively, and the recycling tank is used to collect the xylitol paste that is not converted into the xylitol crystal during centrifugation. By controlling on and off of each valve, switching and control of a series-connection working mode and a parallel-connection working mode is realized for the xylitol exchange liquid in the multiple distribution system.

Further, the xylitol paste that is collected by the recycling tank and not converted into the xylitol crystal is connected to an inlet of J groups of evaporators and a main pipeline holding the xylitol exchange liquid to be treated through an additionally-disposed pipeline, an additionally-disposed valve and a circulation pump disposed in the pipeline so as to be mixed with the to-be-treated xylitol exchange liquid pro rata.

Further, the cleaning liquid collected by the cleaning liquid tank is connected to the main pipeline holding the xylitol exchange liquid to be treated through an additionally-disposed pipeline, an additionally-disposed valve and a cleaning liquid transport pump disposed in the pipeline so as to be mixed with the xylitol exchange liquid pro rata.

The present invention is realized by further providing a control method of the xylitol preparation device integrating evaporation, crystallization and centrifugation as described above. The control method includes the following steps: transporting, through the main pipeline, the xylitol exchange liquid to be treated into the multiple distribution system which firstly obtains the xylitol concentrate by performing evaporation concentration in J groups of evaporators, then obtains the xylitol paste by performing vacuum crystallization in K groups of vacuum crystallization kettles, and then transports the finished xylitol crystal obtained by performing centrifugation in L groups of centrifuges into the xylitol tank for storage. The xylitol paste that is not converted into the xylitol crystal during centrifugation is transported into the recycling tank for temporary recovery, and then connected to the inlet of J groups of evaporators and the main pipeline holding the xylitol exchange liquid to be treated through the additionally-disposed pipeline, the additionally-disposed valve and the circulation pump disposed in the pipeline, so as to be mixed with the xylitol exchange liquid pro rata. The cleaning liquid from cleaning the evaporators, the vacuum kettles and the centrifuges is collected by the cleaning liquid tank for temporary storage through a pipeline and then connected to the main pipeline holding the xylitol exchange liquid to be treated through the additionally-disposed pipeline, the additionally-disposed valve and the cleaning liquid transport pump disposed in the pipeline, so as to be mixed with the xylitol exchange liquid pro rata.

Further, the control method further includes the following step: mixing the xylitol paste that is transported by the circulation pump and not converted into the xylitol crystal with the xylitol exchange liquid in the main pipeline at a ratio of 1:4 for reuse; and mixing the cleaning liquid transported by the cleaning liquid transport pump with the xylitol exchange liquid in the main pipeline at a ratio of 1:8 for reuse.

Further, the xylitol exchange liquid is pre-treated through a coarse filtration process and/or a fine filtration process respectively to remove solid particle impurities. In the coarse filtration process, coarse particle impurities are removed by filtering the xylitol exchange liquid using a filter element with a pore size of 0.45 μm, and a pressure difference during the coarse filtration is controlled between 0.1 MPa and 0.4 MPa. In the fine filtration process, fine particle impurities are removed by filtering the xylitol exchange liquid using a filter element with a pore size of 0.22 μm, and a pressure difference during the fine filtration is controlled between 0.1 MPa and 0.4 MPa.

Further, a transmittance of the xylitol exchange liquid to be treated is 95% or more, its pH value is 5.0-7.5, and its preheating temperature is controlled to 90° C.-100° C.; a refractive index of the xylitol concentrate is 75%-83%, and its temperature is controlled to 55° C.-75° C.

Further, the interior of each centrifuge is cleaned twice by purified water after the centrifuge finishes working, the temperature of the purified water for cleaning is controlled to 40° C.-60° C., and cleaning times are 10 s to 20 s and 5 s to 15 s respectively.

Further, a rotation speed of a stirring motor of the vacuum crystallization kettle is in a range of 300 r/min to 800 r/min, a vacuum degree of the vacuum crystallization kettle is −0.085 MPa to −0.095 MPa, and the vacuum crystallization kettle rapidly reduces the temperature of the xylitol concentrate to a crystallization start temperature of xylitol, i.e. 55° C.-65° C.; a centrifugation time of the centrifuge is 10 min to 30 min.

Further, the evaporator is a triple-effect evaporator including a first-effect evaporator, a second-effect evaporator and a third-effect evaporator. Vacuum degrees of the first-effect evaporator, the second-effect evaporator and the third-effect evaporator are 0.02 MPa to 0.1 MPa, −0.05 MPa to −0.07 MPa and −0.085 MPa to −0.095 MPa respectively, and their evaporation temperatures are controlled to 100° C.-120° C., 90° C.-95° C. and 55° C.-65° C. respectively.

In a xylitol preparation process in the prior art, reaction and separation are connected in series and independent. However, in an actual production process, reaction and separation of xylitol are two major core techniques, which are decisive links for production capacity, cost, energy consumption and emission, and the like. When the reaction and separation of xylitol are connected in series and made independent without control, problems such as many by-products, a poor separation effect, a low utilization rate of raw materials, poor quality and productivity, high energy consumption and emission, and the like may arise. Thus, the present invention provides a xylitol preparation device integrating evaporation, crystallization and centrifugation and a control method thereof, which are characterized below:

A. The entire system is decomposed into a plurality of reaction units and separation units, and is constructed into a plurality of reaction blocks and separation blocks.

B. Selection between blocks and matching functions are realized by controlling switching of electromagnetic valves through a configuration software to realize continuous integrated production.

C. A reaction degree of the reaction unit in each block and a separation degree of the separation unit in each block are selectively controlled by using an intelligent software algorithm based on deep learning to realize optimal coupling of a reaction process and a separation process in different blocks.

In this case, the quality is ensured, and energy saving and emission reduction can also be achieved. Further, products with several target concentrations can be directly obtained by separately controlling the separation unit of each block to reach a different desired separation degree. While flexible production is realized, a process flow is simplified, a production efficiency is improved, and production costs are greatly reduced.

Compared with the prior art, the xylitol preparation device integrating evaporation, crystallization and centrifugation and the control method thereof according to the present invention further have the following features.

(1) The process is environment-friendly and recyclable, the emission is reduced without subsequent troubles, and the raw materials are fully utilized.

(2) The effects of the evaporation, crystallization and centrifugation processes may be enabled to reach optimal distribution by switching the valves, improving the productivity.

(3) The processes and the equipment are highly integrated with low energy consumption and high automation degree, realizing continuous integrated production.

BRIEF DESCRIPTION OF THE DRAWINGS

FIG. 1 is a schematic diagram illustrating a control principle of a xylitol preparation device integrating evaporation, crystallization and centrifugation and a control method thereof according to a preferred embodiment of the present invention.

DETAILED DESCRIPTION OF THE EMBODIMENTS

To understand the technical problems to be solved, technical solutions and beneficial effects of the present invention more clearly, the present invention will be further described in detail below in combination with accompanying drawings and embodiments. It is to be understood that the specific embodiments described herein are only used to explain the present invention rather than limit the present invention.

As shown in FIG. 1, in a preferred embodiment of the present invention, a xylitol preparation device integrating evaporation, crystallization and centrifugation includes a xylitol tank 1, a cleaning liquid tank 2, a recycling tank 3 and a multiple distribution system 4. The multiple distribution system 4 includes J groups of evaporators 5 for evaporation-concentrating a xylitol exchange liquid to be treated into a xylitol concentrate, K groups of vacuum crystallization kettles 6 for obtaining a xylitol paste by vacuum-crystallizing the xylitol concentrate and L groups of centrifuges 7 for obtaining a finished xylitol crystal by centrifuging the xylitol paste, where $2 \leq J \leq 6$, $6 \leq K \leq 12$ and $2 \leq L \leq 4$. Inlets and outlets of the evaporators 5, the vacuum crystallization kettles 6 and the centrifuges 7 in different groups are sequentially connected in series with one another through a pipeline and a valve respectively. The inlets and the outlets of the evaporators 5 in J groups are connected in parallel with each other through a pipeline respectively, the inlets and the outlets of the vacuum crystallization kettles 6 in K groups are connected in parallel with each other through a pipeline respectively, and the inlets and the outlets of the centrifuges in L groups are connected in parallel with each other through a pipeline respectively. The inlet of each evaporator in J groups is in communication with a main pipeline 8 holding the xylitol exchange liquid to be treated through a pipeline and a valve respectively. The outlet of each centrifuge 7 in L groups is in communication with the xylitol tank 1, the cleaning liquid tank 2 and the recycling tank 3 through a pipeline and a valve respectively. The xylitol tank 1 is used to collect the prepared xylitol crystal, the cleaning liquid tank 2 is used to collect cleaning liquid from cleaning the evaporators 5, the vacuum crystallization kettles 6 and the centrifuges 7 respectively, and the recycling tank 3 is used to collect the xylitol paste that is not converted into the xylitol crystal during centrifugation. By controlling on and off of each valve, switching and control of a series-connection working mode and a parallel-connection working mode is realized for the xylitol exchange liquid in the multiple distribution system 4.

The series-connection working mode described herein refers to that the xylitol exchange liquid to be treated firstly enters any evaporator 5 in J groups for evaporation, then enters any vacuum crystallization kettle 6 in K groups for crystallization and then enters any centrifuge 7 in L groups for centrifugation, and then, the obtained xylitol crystal is transported into the xylitol tank 1 for storage.

The parallel-connection working mode described herein refers to that the xylitol exchange liquid to be treated firstly enters two or more parallel-connected evaporators 5 in J groups for simultaneous evaporation, then enters two or more parallel-connected vacuum crystallization kettles 6 in K groups for simultaneous crystallization and then enters two or more centrifuges 7 in L groups for simultaneous centrifugation, and then, the obtained xylitol crystal is transported into the xylitol tank 1 for storage.

The xylitol paste that is collected by the recycling tank 3 and not converted into the xylitol crystal during centrifugation are connected to an inlet of J groups of evaporators 5 and the main pipeline 8 holding the xylitol exchange liquid to be treated through an additionally-disposed pipeline, an additionally disposed valve and a circulation pump 9 disposed in the pipeline so as to be mixed with the xylitol exchange liquid pro rata.

The cleaning liquid collected in the cleaning liquid tank 2 are connected to the main pipeline 8 holding the xylitol exchange liquid to be treated through an additionally-disposed pipeline, an additionally-disposed valve and a cleaning liquid transport pump 10 disposed in the pipeline so as to be mixed with the xylitol exchange liquid pro rata.

The xylitol preparation device further includes a control system, the valves are controlled by electromagnetic valves respectively, and the control system controls the multiple distribution system 4, the xylitol tank 1, the cleaning liquid tank 2, the recycling tank 3 and each electromagnetic valve to realize continuous integrated production of the xylitol crystal. By controlling each valve on the pipelines, the cleaning liquid from cleaning the evaporators 5, the vacuum crystallization kettles 6 and the centrifuges 7 is collected in the cleaning liquid tank for storage, and reusable xylitol paste (i.e., xylose mother liquor) that is generated during centrifugation and not converted into the xylitol crystal are collected in the recycling tank 3 for storage.

The present invention further provides a control method of the xylitol preparation device integrating evaporation, crystallization and centrifugation as described above. The control method includes the following steps: transporting, through the main pipeline 8, the xylitol exchange liquid to be treated into the multiple distribution system 4 which firstly obtains the xylitol concentrate by performing evaporation concentration in J groups of evaporators 5, then obtains the xylitol paste by performing vacuum crystallization in K groups of vacuum crystallization kettles 6, and then transports the finished xylitol crystal obtained after performing centrifugation in L groups of centrifuges 7 into the xylitol tank 1 for storage. The xylitol paste that is not converted into the xylitol crystal during centrifugation is transported into the recycling tank 3 for temporary recovery, then connected to the inlet of J groups of evaporator 5 and the main pipeline 8 holding the xylitol exchange liquid to be treated through the additionally-disposed pipeline, the additionally-disposed valve and the circulation pump 9 disposed in the pipeline, so as to be mixed with the xylitol exchange liquid pro rata. The cleaning liquid from cleaning the evaporators 5, the vacuum crystallization kettles 6 and the centrifuges 7 is collected in the cleaning liquid tank 2 for temporary storage and then connected to the main pipeline 8 holding the xylitol exchange liquid to be treated through the additionally-disposed pipeline, the additionally-disposed valve and the cleaning liquid transport pump 10 disposed in the pipeline, so as to be mixed with the xylitol exchange liquid pro rata.

Specifically, the control method further includes the following step: connecting the cleaning liquid (i.e., xylitol recovered liquid) from regularly cleaning each evaporator 5, each vacuum crystallization kettle 6 and each centrifuge 7 to the cleaning liquid tank 2 for recovery through the additionally-disposed pipeline and additionally-disposed valve. Specifically, the control method further includes the following steps: mixing the xylitol paste that is transported by the circulation pump 9 and not converted into the xylitol crystal with the xylitol exchange liquid in the main pipeline 8 at a ratio of 1:4 for reuse, and mixing the cleaning liquid transported by the cleaning liquid transport pump 10 with the xylitol exchange liquid in the main pipeline 8 at a ratio of 1:8 for reuse.

Specifically, the xylitol exchange liquid to be treated is pre-treated through a coarse filtration process and/or a fine filtration process respectively to remove solid particle impurities. In the coarse filtration process, coarse particle impurities are removed from the xylitol exchange liquid by filtering the xylitol exchange liquid using a filter element with a pore size of 0.45 μm, and a pressure difference during coarse filtration is controlled between 0.1 MPa and 0.4 MPa. In the fine filtration process, fine particle impurities are removed from the xylitol exchange liquid by filtering xylitol exchange liquid using a filter element with a pore size of 0.22 μm, and a pressure difference during fine filtration is controlled between 0.1 MPa and 0.4 MPa.

Specifically, a transmittance of the xylitol exchange liquid to be treated is 95% or more, its PH value is 5.0-7.5, and its preheating temperature is controlled to 90° C.-100° C.; a refractive index of the xylitol concentrate is 75%-83%, and its temperature is controlled to 55° C.-75° C.

Specifically, the interior of each centrifuge 7 is cleaned twice by purified water after the centrifuge finishes working, a temperature of the purified water for cleaning is controlled to 40° C.-60° C., and cleaning times are 10 seconds to 20 seconds and 5 seconds to 15 seconds respectively.

Specifically, a rotation speed of a stirring motor of the vacuum crystallization kettle 6 is in a range of 300 r/min to 800 r/min, a vacuum degree of the vacuum crystallization kettle 6 is −0.085 MPa to −0.095 MPa, and the vacuum crystallization kettle 6 rapidly reduces the temperature of the xylitol concentrate to a crystallization start temperature of xylitol, i.e. 55° C.-65° C.; a centrifugation time of the centrifuge 7 is 10 minutes to 30 minutes.

The centrifuge 7 is cleaned twice with purified water, the temperature of the purified water is controlled to 40° C.-60° C., and the cleaning times are 10 seconds to 20 seconds and 5 seconds to 15 seconds respectively.

Specifically, the evaporator 5 is a triple-effect evaporator including a first-effect evaporator, a second-effect evaporator and a third-effect evaporator, where vacuum degrees of the first-effect evaporator, the second-effect evaporator and the third-effect evaporator are 0.02 MPa to 0.1 MPa, −0.05 MPa to −0.07 MPa and −0.085 MPa to −0.095 MPa respectively, and their evaporation temperatures are controlled to 100° C.-120° C., 90° C.-95° C. and 55° C.-65° C. respectively.

An implementation process and a method of preparing xylitol by integrating evaporation, crystallization and centrifugation are described below in combination with specific embodiments.

1. A process of evaporation-concentrating a xylitol exchange liquid 1.1 In a coarse filtration process of the xylitol exchange liquid, solid impurities contained in the xylitol exchange liquid are coarsely filtered out by a microporous filtration method, that is, coarse particle impurities are removed through a filter element with a pore size of 0.45 μm, and a pressure difference is controlled between 0.1 MPa and 0.4 MPa.

1.2 In a fine filtration process of the xylitol exchange liquid, fine particle impurities are removed through a filter element with a pore size of 0.22 μm, and a pressure difference is controlled between 0.1 MPa and 0.4 MPa. Finally, background colours of filtration membranes of each batch of xylitol exchange liquid samples are controlled, and filtrates are tested according to a criterion; for example, the background colour of the sample membrane is white, a membrane plate is 3 or less, and there is no substance obviously visible to naked eyes, thus evaporation concentration can be performed.

1.3 After a vacuum pump is started, when the vacuum degree of the evaporator 5 reaches −0.08 MPa or above, feeding is started, and a steam valve is opened at the same time for evaporation concentration.

1.4 The evaporation is performed by the evaporator 5, and a material firstly passes through a plate-type preheating system at a preheating temperature controlled to 90° C.-100° C. The material reaches the evaporator of each effect for evaporation through a liquid transport pump of each effect, and then enters the vacuum crystallization kettle 6.

1.5 In the evaporation process, the vacuum degree of the first-effect evaporator is 0.02 MPa to 0.1 MPa, and the temperature of the material is 100° C.-120° C.; the vacuum degree of the second-effect evaporator is −0.05 MPa to −0.07 MPa, and the temperature of the material is 90° C.-100° C.; the vacuum degree of the third-effect evaporator is −0.085 MPa to −0.095 MPa, the temperature of the material is 55° C.-65° C., and the refractive index of the material is between 75% and 83%.

1.6 After the evaporation concentration process is completed, the evaporator 5 is cleaned with purified water to prevent fouling and clogging. The cleaning water is discharged into the cleaning liquid tank 2 for recycling.

2. Vacuum crystallization process 2.1 The vacuum crystallization process is a crystallization manner in which a part of moisture in the xylitol concentrate is taken away by vacuumization to increase the concentration of the xylitol concentrate and reduce the temperature of the material simultaneously during crystallization, thereby accelerating crystallization of xylitol from the xylitol concentrate.

2.2 Feeding: during feeding, a jacket of the vacuum crystallization kettle 6 is heated to 60° C.-80° C. in advance; when the xylitol concentrate reaches a first sight glass of the vacuum crystallization kettle 6, the vacuum crystallization kettle 6 is started for stirring, with a motor speed controlled to 400 r/min-800 r/min.

2.3 Crystallization: the vacuum degree of the vacuum crystallization kettle 6 is controlled between −0.085 MPa and −0.095 MPa and the temperature is rapidly lowered to the crystallization start temperature 55° C.-65° C. In the crystallization process, the temperature of the xylitol concentrate is controlled within a range of 55° C.-75° C.

2.4 After the crystallization is completed, a jacketed steam valve of a crystallization assistance tank is opened to control the temperature of the jacket to be approximate to the temperature of the material (a difference of ±5° C. compared with the temperature of the material) in the vacuum crystallization kettle 6 at this time; then, the vacuum of the vacuum crystallization kettle 6 is relieved through a vacuum relief valve, and a feed valve of the vacuum crystallization kettle 6 is opened to discharge the material into the centrifuge 7 for separation through the crystallization assistance tank.

2.5 After the crystallization process is completed, the vacuum crystallization kettle 6 is cleaned by purified water to prevent fouling and clogging. The cleaning water is discharged into the cleaning liquid tank 2 for recycling.

3. Centrifugation process 3.1 After a notification of a previous procedure is received, relevant preparation is to be made to ensure a normal operation of the centrifuge 7.

3.2 A control button is set to an automatic level for use of automatic control program. After a feed button is depressed, the previous procedure is notified of feeding material to perform a centrifugal crystallization process of the xylitol paste. After liquid removal is performed for 2 minutes, a cleaning switch is turned on to clean the xylitol paste in the centrifuge twice with purified water for a total of 25 seconds (one cleaning is 15 seconds, and the other cleaning is 10 seconds), the temperature of the purified water is controlled to 40° C.-60° C., and a time of each centrifugation is controlled between 10 minutes and 30 minutes.

3.3 After the centrifugation is completed, the xylitol crystal is transported into the xylitol tank 1 for storage, the xylitol paste that is not converted into the xylitol crystal is transported into the recycling tank 3 and then transported into the pipeline holding the xylitol exchange liquid to be treated through the circulation pump 9 and the cleaning liquid transport pump 10 so as to be mixed with the xylitol exchange liquid pro rata. The centrifuge 7 is cleaned by the purified water to prevent fouling and clogging. The cleaning water is discharged into the cleaning liquid tank 2 for recycling.

The method of the present invention is further described below in combination with specific embodiments.

Embodiment 1

In this embodiment, the multiple distribution system included two groups of evaporators 5 with a water evaporation capacity of each group being 2 tons/hour, 8 vacuum crystallization kettles 6 with a volume being 15 m³/pcs, and 2 top-suspended centrifuges 7 with a model being XG-1250AT. In this embodiment, a xylitol crystal production capacity of the device was 3 tons/hour to 4 tons/hour.

In this embodiment, the device prepared the xylitol through the following process:

The xylitol exchange liquid was firstly filtered using a filter element with a pore size of 0.45 μm to remove coarse particle impurities with a pressure difference controlled between 0.1 MPa and 0.4 MPa, and then finely filtered using a filter element with a pore size of 0.22 μm. Evaporation concentration may be performed when there is no substance obviously visible to naked eyes.

A vacuum pump of the evaporator 5 was started. After the vacuum degree of the evaporator 5 reached −0.08 MPa, an evaporation feed pump and an evaporator return valve were started. A steam valve was opened to perform evaporation concentration after the return valve discharges material. The pressure difference was adjusted to allow the material to enter the evaporator 5 of each effect sequentially to perform evaporation concentration sequentially. After an online mass flowmeter detected the concentration reached 82%, a discharge valve was automatically opened with the return valve automatically closed, and a feed valve of a corresponding vacuum crystallization kettle 6 was opened in advance to allow the xylitol concentrate to enter the vacuum crystallization kettle 6.

In the vacuum crystallization process, the jacket of the vacuum crystallization kettle 6 was heated in advance. When the xylitol concentrate entered the vacuum crystallization kettle 6, stirring was started with a controlled rotation speed of the motor, then the vacuum crystallization kettle 6 is vacuumized to −0.085 MPa, and then, cooled down to achieve the purpose of crystallization. After that, the xylitol paste was obtained and then transported into the centrifuge 7 for performing centrifugation operation for the xylitol paste with a time of each centrifugation controlled to around 15 minutes. In this way, the xylitol crystal, the xylitol paste that was not converted into the xylitol crystal (i.e., primary xylitol crystallization mother liquor) and a centrifugal cleaning liquid were obtained.

The obtained xylitol crystal (xylitol content was 99.5% or more) was transported into the xylitol tank. The obtained primary xylitol crystallization mother liquor (xylitol content was around 89% and sugar concentration was around 50%) was transported into the recycling tank 3, and then transported into the pipeline holding the xylitol exchange liquid to be treated through the circulation pump 9 so as to be mixed with the xylitol exchange liquid at a ratio of 1:4. The obtained centrifugal cleaning liquid (xylitol content was around 95% and sugar concentration was around 5%) was transported into the cleaning liquid tank 2, and then transported into the pipeline holding the xylitol exchange liquid to be treated through the cleaning liquid pump 10 so as to be mixed with the xylitol exchange liquid at a ratio of 1:8.

When treatment was performed by adopting the device and the method of the present invention, 1.03 tons of crystal xylose (xylose content was 99% or more and moisture was less than 0.5%) were consumed for producing 1 ton of xylitol crystal (xylitol content was 99.5% or more and moisture was less than 0.5%), saving around 3% compared with the prior art; 2.0 tons of steam (steam pressure was 0.6 MPa to 0.8 MPa) were consumed for producing 1 ton of xylitol crystal, saving around 8% compared with the prior art; a primary crystallization yield of the xylitol crystal was 50% or more, increasing by 5% or more compared with the prior art.

Embodiment 2

In this embodiment, the multiple distribution system included three groups of evaporators 5 with the water evaporation capacity of each group being 3 tons/hour, 14 vacuum crystallization kettles 6 with the volume being 20 m³/pcs, and 4 top-suspended centrifuges 7 with model being XG-1250AT. In this embodiment, the xylitol crystal production capacity of the device was 6 tons/hour to 10 tons/hour.

In this embodiment, the device prepared the xylitol through the following process.

The xylitol exchange liquid was firstly filtered using a filter element with a pore size of 0.45 μm to remove coarse particle impurities with a pressure difference controlled between 0.1 MPa and 0.4 MPa, and then finely filtered using a filter element with a pore size of 0.22 μm. Evaporation concentration may be performed when there was no substance obviously visible to naked eyes.

A vacuum pump of the evaporator 5 was started. After the vacuum degree of the evaporator 5 reached −0.08 MPa, an evaporation feed pump and an evaporator return valve were started. A steam valve was opened to perform evaporation concentration after the return valve discharges material. The pressure difference was adjusted to allow the material to enter the evaporator 5 of each effect sequentially to perform evaporation concentration sequentially. After an online mass flowmeter detected the concentration reached 82%, a discharge valve was automatically opened with the return valve automatically closed, and a feed valve of a corresponding vacuum crystallization kettle 6 was opened in advance to allow the xylitol concentrate to enter the vacuum crystallization kettle 6.

In the vacuum crystallization process, the jacket of the vacuum crystallization kettle 6 was heated in advance. When the xylitol concentrate entered the vacuum crystallization kettle 6, stirring was started with a controlled rotation speed of the motor, then the vacuum crystallization kettle 6 is vacuumized to −0.085 MPa, and then cooled down to achieve the purpose of crystallization. After that, the xylitol paste was obtained and then transported into the centrifuge 7 for performing centrifugation operation for the xylitol paste with a time of each centrifugation controlled to around 15 minutes. In this way, the xylitol crystal, the xylitol paste that was not converted into the xylitol crystal (i.e., primary xylitol crystallization mother liquor) and a centrifugal cleaning liquid were obtained.

The obtained xylitol crystal (xylitol content was 99.5% or more) was transported into the xylitol tank. The obtained primary xylitol crystallization mother liquor (xylitol content was around 89% and sugar concentration was around 50%) was transported into the recycling tank 3, and then transported into the pipeline holding the xylitol exchange liquid to be treated through the circulation pump 9 so as to be mixed with the xylitol exchange liquid at the ratio of 1:4. The obtained centrifugal cleaning liquid (xylitol content was around 95% and sugar concentration was around 5%) was transported into the cleaning liquid tank 2, and then transported into the pipeline holding the xylitol exchange liquid to be treated through the cleaning liquid pump 10 so as to be mixed with the xylitol exchange liquid at the ratio of 1:8.

When the treatment was performed by adopting the device and the method of the present invention, 1.03 tons of crystal xylose (xylose content was 99% or more and moisture was less than 0.5%) were consumed for producing 1 ton of xylitol crystals (xylitol content was 99.5% or more and moisture was less than 0.5%), saving around 3% compared with the prior art; 2.0 tons of steam (steam pressure was 0.6 MPa to 0.8 MPa) were consumed for producing 1 ton of xylitol crystal, saving around 8% compared with the prior art; the primary crystallization yield of the xylitol crystal was 50% or more, increasing by 5% or more compared with the prior art.

Embodiment 3

Firstly, the xylitol exchange liquid underwent a coarse filtration and a fine filtration to remove particle impurities. The exchange liquid was filtered using a filter element with a pore size of 0.45 μm in the coarse filtration process with a pressure difference controlled between 0.1 MPa and 0.4 MPa, and then filtered using a filter element with a pore size of 0.22 μm in the fine filtration process with a pressure difference controlled between 0.1 MPa and 0.4 MPa. In this case, it was ensured that the xylitol mother liquor was not consumed during filtration while large-particle crystals were filtered out completely, thereby avoiding losses.

Then, the obtained xylitol exchange liquid was detected. When a transmittance of the xylitol exchange liquid reached 95% or more and its PH value was between 5.0 and 7.5, the next operation was performed to detect a filtration effect of the xylitol exchange liquid. After that, a preheating operation was performed for the xylitol exchange liquid at a temperature controlled between 90° C. and 100° C. to obtain a primary xylitol concentrate with a refractive index being 73%-83% which is then cooled down to 55° C.-75° C. for the next operation. The first concentration belonged to a normal pressure process with a purpose of performing a preheating procedure before entry into the evaporator 5 so as to facilitate the next operation. Then, the xylitol mother liquor was evaporation-concentrated through the evaporator 5 and the vacuum crystallization kettle 6. Opening and closing of the valves were controlled according to a xylitol mother liquor quantity and a pressure change. When the vacuum degree was 0.02 MPa to 0.1 MPa, −0.05 MPa to −0.07 MPa and −0.085 MPa to −0.095 MPa respectively, the temperature was adjusted to 100° C.-120° C., 90° C.-95° C. and 55° C.-65° C. respectively. The corresponding valve was also opened in a temperature interval. The centrifuge 7 was started when a secondary concentrated mother liquor in the evaporator 5 entered the vacuum crystallization kettle 6, and the centrifugation time was 10 minutes to 30 minutes when the xylitol crystallization temperature reached 55° C.-65° C. Then, the jacketed steam valves of the crystallization assistance tanks were opened sequentially to perform de-vacuumization so as to separate crystal substances from the vacuum crystallization kettle 6 better.

After the vacuum crystallization kettle 6 completed crystallization, the obtained xylitol paste was transported into the centrifuge 7. The centrifuge 7 was started only when receiving information that the jacketed steam valve of the crystallization assistance tank was opened. After the feed button was depressed, the centrifugal crystallization process was performed for the xylitol paste for 10 minutes-20 minutes, and the obtained centrifugate, i.e., xylitol crystal, was transported into the xylitol tank 1 sequentially and collected as finished products. A centrifugal sugar paste cleaning liquid was transported into the cleaning liquid tank 2, and then mixed with a primary liquid at a ratio of 1:8 for the next evaporation crystallization process. The xylitol paste that was not converted into the xylitol crystal was transported into the recycling tank 3 and then directly transported back to the xylitol exchange liquid for the evaporation crystallization operation.

In the entire process, it was required to dispose a cleaning pipeline for cleaning all pipelines with purified water, where the temperature of the purified water was 40° C.-60° C. It was required to perform residue cleaning for 15 seconds and tank cleaning for 10 seconds respectively to prevent fouling and clogging.

Integrated control of the entire process is optimized by fully considering a physical change process of xylitol crystallization. In actual production, operation and control may be performed completely according to the above process. An operation method of regioselective integrated control performed in the production process obviously saves energy consumption and also enables the production process to be more efficient, high-quality, clean and reasonable, and the like Process control indicators of the xylitol preparation device integrating evaporation, crystallization and centrifugation according to the present invention are as follows:

| Procedure name | Material name | Control item | Control indicator | Control frequency |
| --- | --- | --- | --- | --- |
| Evaporation | Xylitol exchange liquid | Water-insoluble substance | Background colour of sample membrane is white with no substance obviously visible to naked eyes. | Once for each batch |
| Crystallization | Xylitol concentrate | Refractive index | 75-83% | Once for each batch |
| Centrifugation | Xylitol crystal | Content | ≥99.8% | Once for each batch |

Main parameters of the vacuum crystallization kettle adopted by the present invention are as follows:

| Volume | 9.4 m³ | | Container height | 3400 mm | |
| --- | --- | --- | --- | --- | --- |
| Design pressure | Inner cylinder | −0.1 MPa | Actual operation pressure | Inner cylinder | −0.1 MPa |
| | Jacket | 0.4 MPa | | Jacket | 0.2 MPa |
| Design temperature | Inner cylinder | 120° C. | Actual operation temperature | Inner cylinder | <120° C. |
| | Jacket | 151° C. | | Jacket | 151° C. |

Process parameters of the centrifuge adopted by the present invention are as follows:

| Model (mm) | Drum diameter | Drum height (mm) | Drum volume (L) | Feed limit (Kg) | Maximum rotation speed (r/min) | Maximum separating factor | Motor power (Kw) | Machine weight (Kg) |
|---|---|---|---|---|---|---|---|---|
| SGZ-1250 | 1250 | 500/630/800 | 310/400/505 | 400/520/650 | 1000 | 698 | 18.5/22 | 4850/5000/6000 |

The above descriptions are merely preferred embodiments of the present invention to which the present invention is not limited. Any modifications, equivalent substitutions and improvements, and the like made within the spirit and the principle of the present invention shall all fall in the scope of protection of the present invention.

The invention claimed is:

1. A xylitol preparation device integrating evaporation, crystallization and centrifugation, comprising a xylitol tank, a cleaning liquid tank, a recycling tank, and a multiple distribution system,
    wherein the multiple distribution system comprises J groups of evaporators for evaporation-concentrating a xylitol exchange liquid to be treated into a xylitol concentrate, K groups of vacuum crystallization kettles for obtaining a xylitol paste by vacuum-crystallizing the xylitol concentrate, and L groups of centrifuges for obtaining a xylitol crystal by centrifuging the xylitol paste, wherein $2 \leq J \leq 6$, $6 \leq K \leq 12$ and $2 \leq L \leq 4$;
    inlets and outlets of the evaporator, the vacuum crystallization kettle and the centrifuge in different groups are sequentially connected in series with one another through a pipeline and a valve respectively, inlets and outlets of the evaporators in J groups are connected in parallel with each other through a pipeline respectively, inlets and outlets of the vacuum crystallization kettles in K groups are connected in parallel with each other through a pipeline respectively, inlets and outlets of the centrifuges in L groups are connected in parallel with each other through a pipeline respectively, the inlet of each evaporator in J groups is in communication with a main pipeline holding the xylitol exchange liquid to be treated through a pipeline and a valve respectively, and the outlet of each centrifuge in L groups is in communication with the xylitol tank, the cleaning liquid tank and the recycling tank through a pipeline and a valve respectively;
    the xylitol tank is configured to collect the prepared xylitol crystal, the cleaning liquid tank is configured to collect cleaning liquid from cleaning the evaporators, the vacuum crystallization kettles and the centrifuges respectively, and the recycling tank is configured to collect the xylitol paste that is not converted into the xylitol crystal during centrifugation; and
    the multiple distribution system is configured to switch the xylitol exchange liquid between a series-connection working mode and a parallel-connection working mode by controlling on and off of each valve.

2. The xylitol preparation device according to claim 1, wherein the device is configured to transport the xylitol paste that is collected by the recycling tank and not converted into the xylitol crystal to the inlet of J groups of evaporators and the main pipeline holding the xylitol exchange liquid to be treated through an additionally-disposed pipeline, an additionally-disposed valve and a circulation pump disposed in the pipeline so as to be mixed with the xylitol exchange liquid pro rata.

3. The xylitol preparation device according to claim 1, wherein the device is configured to transport the cleaning liquid collected in the cleaning liquid tank to the main pipeline holding the xylitol exchange liquid to be treated through an additionally-disposed pipeline, an additionally-disposed valve and a cleaning liquid transport pump disposed in the pipeline so as to be mixed with the xylitol exchange liquid pro rata.

4. A method of operating the xylitol preparation device according to any one of claim 1, comprising the following steps:
    transporting the xylitol exchange liquid to be treated, through the main pipeline, into the multiple distribution system;
    obtaining the xylitol concentrate by performing evaporation concentration in the J groups of evaporators;
    obtaining the xylitol paste by performing vacuum crystallization in the K groups of vacuum crystallization kettles;
    obtaining the xylitol crystal by performing centrifugation in the L groups of centrifuges; and
    transporting the xylitol crystal into the xylitol tank for storage;
    wherein the xylitol paste that is not converted into the xylitol crystal during centrifugation is transported into the recycling tank for temporary recovery and then to the inlet of J groups of evaporators and the main pipeline holding the xylitol exchange liquid to be treated through the additionally-disposed pipeline, the additionally-disposed valve and the circulation pump disposed in the pipeline, so as to be mixed with the xylitol exchange liquid pro rata; and
    the cleaning liquid from cleaning the evaporators, the vacuum kettles and the centrifuges is collected in the cleaning liquid tank for temporary storage through the pipeline and transported to the main pipeline holding the xylitol exchange liquid to be treated through the additionally-disposed pipeline, the additionally-disposed valve and the cleaning liquid transport pump disposed in the pipeline, so as to be mixed with the xylitol exchange liquid pro rata.

5. The method according to claim 4, further comprising the following step:
    mixing the xylitol paste that is transported by the circulation pump and not converted into the xylitol crystal with the xylitol exchange liquid in the main pipeline at a ratio of 1:4 for reuse; and
    mixing the cleaning liquid transported by the cleaning liquid transport pump with the xylitol exchange liquid in the main pipeline at a ratio of 1:8 for reuse.

6. The method according to claim 4, wherein the xylitol exchange liquid to be treated is pre-treated through a coarse filtration process and/or a fine filtration process respectively to remove solid particle impurities;
    in the coarse filtration process, coarse particle impurities are removed from the xylitol exchange liquid by adopting a filter element with a pore size of 0.45 μm, and a pressure difference during the coarse filtration is controlled between 0.1 MPa and 0.4 MPa; and in the fine filtration process, fine particle impurities are removed from the xylitol exchange liquid by adopting a filter element with a pore size of 0.22 μm, and a pressure difference during the fine filtration is controlled between 0.1 MPa and 0.4 MPa.

7. The method according to claim 4, wherein a transmittance of the xylitol exchange liquid to be treated is 95% or more, a PH value is 5.0-7.5, and a preheating temperature is controlled to 90° C.-100° C.; a refractive index of the xylitol concentrate is 75%-83%, and a temperature is controlled to 55° C.-75° C.

8. The method according to claim 4, wherein the interior of each centrifuge is cleaned twice by purified water after the centrifuge finishes working, a temperature of the purified water for cleaning is controlled to 40° C.-60° C. and cleaning times are 10 seconds to 20 seconds and 5 seconds to 15 seconds respectively.

9. The method according to claim 4, wherein a rotation speed of a stirring motor of the vacuum crystallization kettle is in a range of 300 r/min to 800 r/min, a vacuum degree of the vacuum crystallization kettle is −0.085 MPa to −0.095 MPa, and the vacuum crystallization kettle cools down the xylitol concentrate to a crystallization start temperature of xylitol of 55° C.-65° C.; a centrifugation time of the centrifuge is 10 minutes to 30 minutes.

10. The method according to claim 4, wherein the evaporator is a triple-effect evaporator comprising a first-effect evaporator, a second-effect evaporator and a third-effect evaporator, vacuum degrees of the first-effect evaporator, the second-effect evaporator and the third-effect evaporator are 0.02 MPa to 0.1 MPa, −0.05 MPa to −0.07 MPa and −0.085 MPa to −0.095 MPa respectively, and evaporation temperatures of the three evaporators are controlled to 100° C.-120° C., 90° C.-95° C. and 55° C.-65° C. respectively.

* * * * *